US005261410A

United States Patent [19]
Alfano et al.

[11] Patent Number: 5,261,410
[45] Date of Patent: Nov. 16, 1993

[54] METHOD FOR DETERMINING IF A TISSUE IS A MALIGNANT TUMOR TISSUE, A BENIGN TUMOR TISSUE, OR A NORMAL OR BENIGN TISSUE USING RAMAN SPECTROSCOPY

[76] Inventors: Robert R. Alfano, 3777 Independence Ave., Bronx, N.Y. 10463; Cheng H. Liu, 140-25 Ash Ave., Apt. 3A, Flushing, N.Y. 11355; Wenling S. Glassman, 104 Terrace View Ave., Apt. 2N, Bronx, N.Y. 10463

[21] Appl. No.: 651,449

[22] Filed: Feb. 7, 1991

[51] Int. Cl.$^5$ ............................................... A61B 6/00
[52] U.S. Cl. .................................... 128/664; 250/339; 250/341
[58] Field of Search ............... 128/664, 665, 395, 397, 128/398; 356/301; 250/339–341

[56] References Cited
U.S. PATENT DOCUMENTS

| | | | |
|---|---|---|---|
| 4,718,417 | 1/1988 | Kittrell et al. | 128/634 |
| 4,832,483 | 5/1989 | Verma | 128/665 |
| 4,930,516 | 6/1990 | Alfano et al. | 128/665 |
| 5,168,162 | 12/1992 | Dong et al. | 250/339 |
| 5,197,470 | 3/1993 | Helfer et al. | 128/664 |

Primary Examiner—Ruth S. Smith
Attorney, Agent, or Firm—Kriegsman & Kriegsman

[57] ABSTRACT

A method for determining if a tissue is a malignant tumor tissue, a benign tumor tissue, or a normal or benign tissue. The present method is based on the discovery that, when irradiated with a beam of infrared, monochromatic light, malignant tumor tissue, benign tumor tissue, and normal or benign tissue produce distinguishable Raman spectra. For human breast tissue, some salient differences in the respective Raman spectra are the presence of four Raman bands at a Raman shift of about 1078, 1300, 1445, and 1651 cm$^{-1}$ for normal or benign tissue, the presence of three Raman bands at a Raman shift of about 1240, 1445, and 1659 cm$^{-1}$ for benign tumor tissue, and the presence of two Raman bands at a Raman shift of about 1445 and 1651 cm$^{-1}$ for malignant tumor tissue. In addition, it was discovered that for human breast tissue the ratio of intensities of the Raman bands at a Raman shift of about 1445 and 1659 cm$^{-1}$ is about 1.25 for normal or benign tissue, about 0.93 for benign tumor tissue, and about 0.87 for malignant tumor tissue.

16 Claims, 6 Drawing Sheets

METHOD FOR DETERMINING IF A TISSUE IS A MALIGNANT TUMOR TISSUE, A BENIGN TUMOR TISSUE, OR A NORMAL OR BENIGN TISSUE USING RAMAN SPECTROSCOPY

BACKGROUND OF THE INVENTION

The present invention relates to a method for determining if a tissue is a malignant tumor tissue, a benign tumor tissue, or a normal or benign tissue using Raman spectroscopy.

Because a sufficiently effective method for preventing cancer has not yet been developed, cancer research has focused on the most effective ways to treat organisms that are diagnosed as having cancer. As different as the various forms of treatment have been—ranging from excision to radiation to chemotherapy—all treatments have relied on one crucial step, detection of the cancerous tissue. If cancer is detected early enough, it may be possible to determine where in the body the cancer originated. This information may be useful in deciding on the most safe and effective treatment for the cancer.

Typically, cancer occurs when a normal cell undergoes a change which causes the cell to multiply at a metabolic rate for exceeding that of its neighboring cells. Continued multiplication of the cancerous cell frequently results in the creation of a mass of cells called a tumor. Cancerous tumors are harmful because they grow at the expense of normal neighboring cells, ultimately destroying them. In addition, cancerous cells are often capable of traveling throughout the body via the lymphatic and circulatory systems and of creating new tumors where they arrive. Consequently, the importance of detecting a cancer before the cancer has spread to diverse portions of the body cannot be minimized.

It should be noted that, in addition to tumors which are cancerous (also referred to as malignant tumors), there are tumors which are non-cancerous. Non-cancerous tumors are commonly referred to as benign tumors. For the reasons discussed earlier, it is useful to be able to determine whether a tumor is cancerous or benign.

SUMMARY OF THE INVENTION

It is an object of the present invention to provide a new and improved technique for determining if a tissue is a malignant tumor tissue, a benign tumor tissue, or a normal or benign tissue.

It is another object of the present invention to provide a new and improved technique for determining if a tumor tissue is a malignant tumor tissue or a benign tumor tissue.

It is a further object of the present invention to provide a technique for detecting cancerous tissue which does not require the use of X-ray sensitive plates or photodetectors and does not involve the use of fluorescence or ultrasound.

It is still a further object of the present invention to provide a technique for detecting malignant tumor tissue which can be used either in vivo or in vitro.

The present invention is based on the surprising discovery that malignant tumor tissue, benign tumor tissue, and normal or benign tissue produce distinguishable infrared Raman spectra when irradiated with a beam of monochromatic infrared light. Infrared Raman spectroscopy, as opposed to ultraviolet or visible Raman spectroscopy, is used herein because biological tissues typically have very large ultraviolet and visible fluorescence backgrounds which overwhelm the ultraviolet and visible Raman spectra.

In accordance with the teachings of the present invention, malignant human breast tumor tissue, benign human breast tumor tissue and benign human breast tissue were irradiated with a beam of monochromatic infrared light and the respective infrared Raman spectra were obtained. These spectra showed four characteristic Raman bands at a Raman shift of about 1078, 1300, 1445 and 1651 cm$^{-1}$ for the benign tissue, three characteristic Raman bands at a Raman shift of about 1240, 1445, and 1659 cm$^{-1}$ for the benign tumor tissue, and two characteristic Raman bands at a Raman shift of about 1445 and 1651 cm$^{-1}$ for the malignant tumor tissue. In addition, the intensity ratios of the two common characteristic Raman bands at a Raman shift of about 1445 and 1651 cm$^{-1}$ were found to be less than 0.9 for the malignant tumor tissue, about 0.93 for the benign tumor tissue, and about 1.25 for the benign tissue.

Accordingly, a method for determining if a tissue is a malignant tumor tissue, a benign tumor tissue, or a normal or benign tissue comprises in one embodiment irradiating the tissue with a beam of infrared monochromatic light, obtaining the infrared Raman spectrum for the tissue, and comparing said infrared Raman spectrum with standard infrared Raman spectra from malignant tumor tissue, benign tumor tissue, and normal or benign tissue for the same type of tissue being tested.

In another embodiment, a method for determining if a tissue is a malignant tumor tissue, a benign tumor tissue, or a normal or benign tissue comprises irradiating the tissue with a beam of infrared monochromatic light, measuring the intensity of two characteristic Raman bands common to the infrared Raman spectra for malignant tumor tissue, benign tumor tissue, and normal or benign tissue for the same type of tissue being tested, calculating the ratio of said intensities, and comparing said ratio to the respective ratios for malignant tumor tissue, benign tumor tissue, and normal or benign tissue for the same type of tissue being tested.

The method of the present invention can be used to distinguish malignant tumor tissue, benign tumor tissue, and benign or normal tissue for tissues obtained from various parts of the human body including the cervix, the uterus, the ovaries, the rectum, the colon, the brain, the bladder, the skin, the breast, the stomach, the lung, and the mouth.

The foregoing and other objects and advantages will appear from the description to follow. In the description, reference is made to the accompanying drawing which forms a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

DETAILED DESCRIPTION OF PREFERRED EMBODIMENTS

The present invention is directed to a method for determining if a tissue is a malignant tumor tissue, a benign tumor tissue, or a normal or benign tissue. (For purposes of the present invention, normal tissue and benign tissue are considered to be indistinguishable.)

The present invention is based on the above-noted discovery that, when irradiated with a beam of monochromatic infrared light, malignant tumor tissue, benign tumor tissue, and normal or benign tissue produce distinguishable Raman spectra. Therefore, by comparing the infrared Raman spectra from a sample tissue whose condition is unknown with standard infrared Raman spectra obtained from malignant tumor tissue, benign tumor tissue, and normal or benign tissue for the same type of tissue being tested (i.e., breast tissue is compared to breast tissue standards, uterus tissue is compared to uterus tissue standards, etc.), it is possible to determine if the tissue sample being tested is a malignant tumor tissue, a benign tumor tissue, or a normal or benign tissue. The types of comparisons that can be made are numerous. For example, one can compare the number of characteristic Raman lines in the infrared Raman spectrum for the tissue being tested with the number of characteristic Raman lines in standard infrared Raman spectra obtained from malignant tumor tissue, benign tumor tissue, and normal or benign tissue. As another example, one can compare the ratio of intensities of two characteristic Raman lines which are common to the infrared Raman spectra for malignant tumor tissue, benign tumor tissue, and normal or benign tissue for the same type of tissue being tested with the respective ratios for malignant tumor tissue, benign tumor tissue, and normal or benign tissue for the same of type of tissue being tested.

Figure 1:
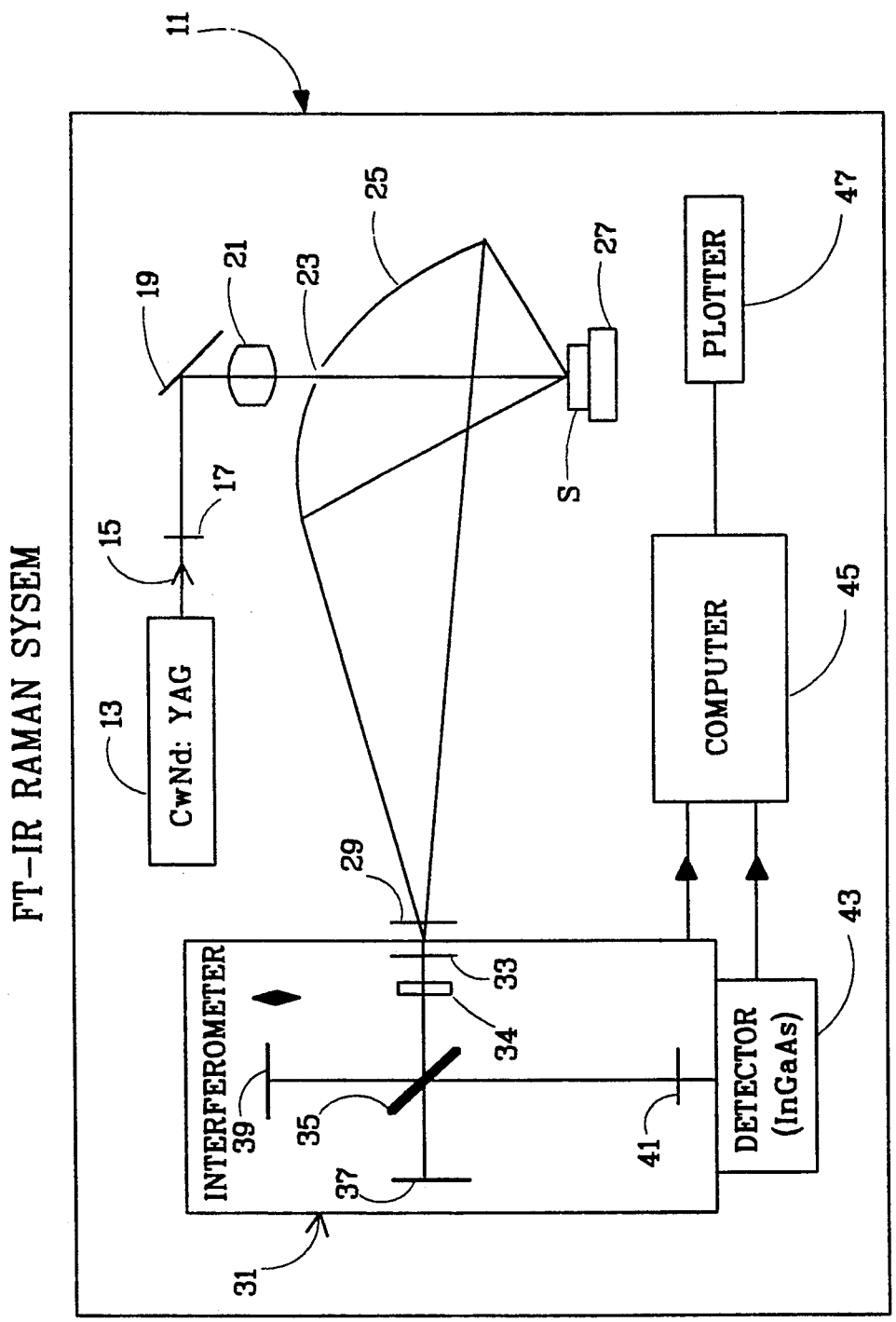
FIG. 1 is a schematic diagram of an infrared Fourier Transform Raman spectroscopy system which can be used to perform the method of the present invention.

Referring now to FIG. 1, there is shown a schematic diagram of a system which was used to perform the method of the present invention, the system being represented generally by reference numeral 11.

System 11 includes a laser 13 for generating a beam of monochromatic infrared light 15. Laser 13 may be any tunable infrared laser capable of emitting light at about 680-1350 nanometers (nm). For example, laser 13 may be a semiconductor, fosterite, YAG, Ti sapphire, alexandrite, emerald, GGSG or dye laser. Preferably, laser 13 is a Quantronix model 114 Nd:YAG laser producing linear polarized $TEM_{00}$ infrared radiation at 1064 nm of about 1 watt power.

Beam 15 passes through a combination narrow-band, wide-band, and neutral density filter unit 17, is reflected off a mirror 19 and is focused by a lens 21 through a hole 23 in an on-axis ellipsoidal mirror 25 onto a sample S, which is mounted on a holder 27. Preferably holder 27 is a three-dimensional adjustable slide in a glass tube. Upon striking sample S, the beam of light is scattered in accordance with the Raman effect. The scattered light strikes ellipsoidal mirror 25, where it is collected and brought to focus onto a filter 29, which blocks out radiation at 1064 nm at the entrance to a conventional Michelson interferometer 31. On entering interferometer 31, the beam passes through a filter 33 which is further constructed to block out radiation at 1064 nm. Next, the beam is collimated by a collimator 34 and then split into two beams by a $CaF_2$ beam splitter 35. One beam is reflected off a fixed mirror 37, and the other beam is reflected off a movable mirror 39. The two beams are recombined at beam splitter 35 and pass through a neutral density filter 41.

The resultant interference pattern produced by interferometer 31 is detected with a liquid nitrogen-cooled indium-gallium-arsenide photodiode-type detector 43. The information is then processed with a computer 45 and displayed as a Raman spectrum on a plotter 47.

System 11 may comprise a modified Bomem DA 3.16 FT-Raman spectrophotometer, distributed by Bomem, Inc. having a place of business in Newark, Del.

Figure 2:
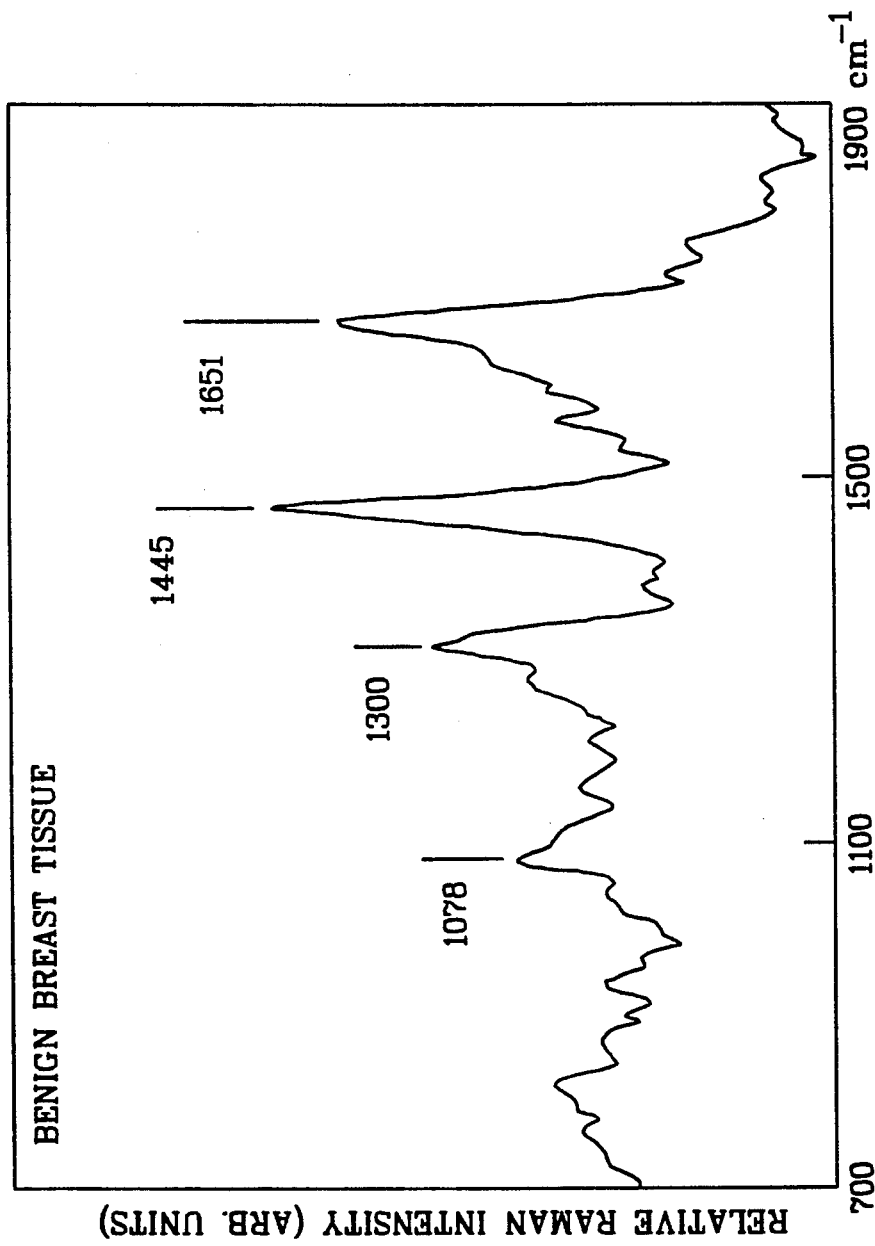
FIG. 2 is a Raman spectrum obtained from benign tissue.
Figure 3:
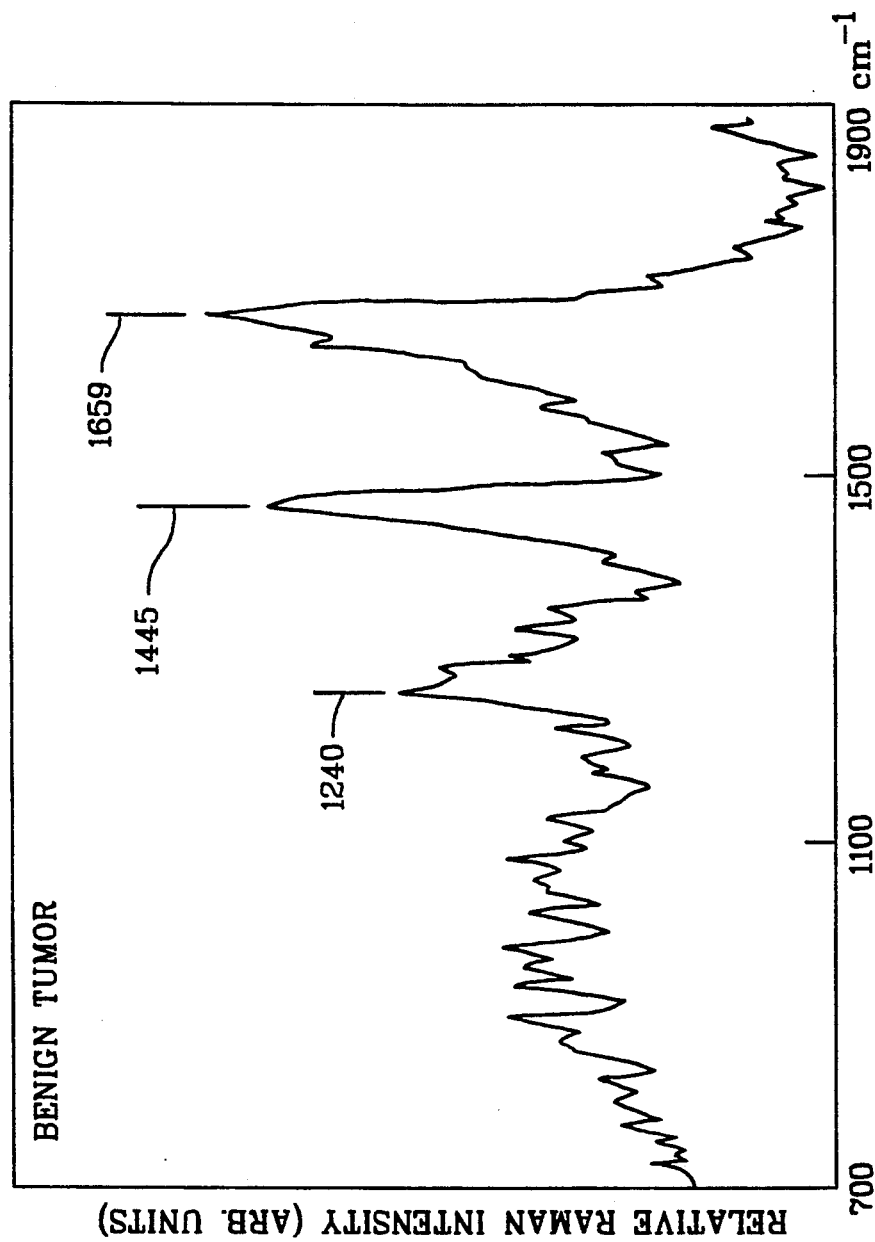
FIG. 3 is a Raman spectrum obtained from benign tumor tissue.
Figure 4:
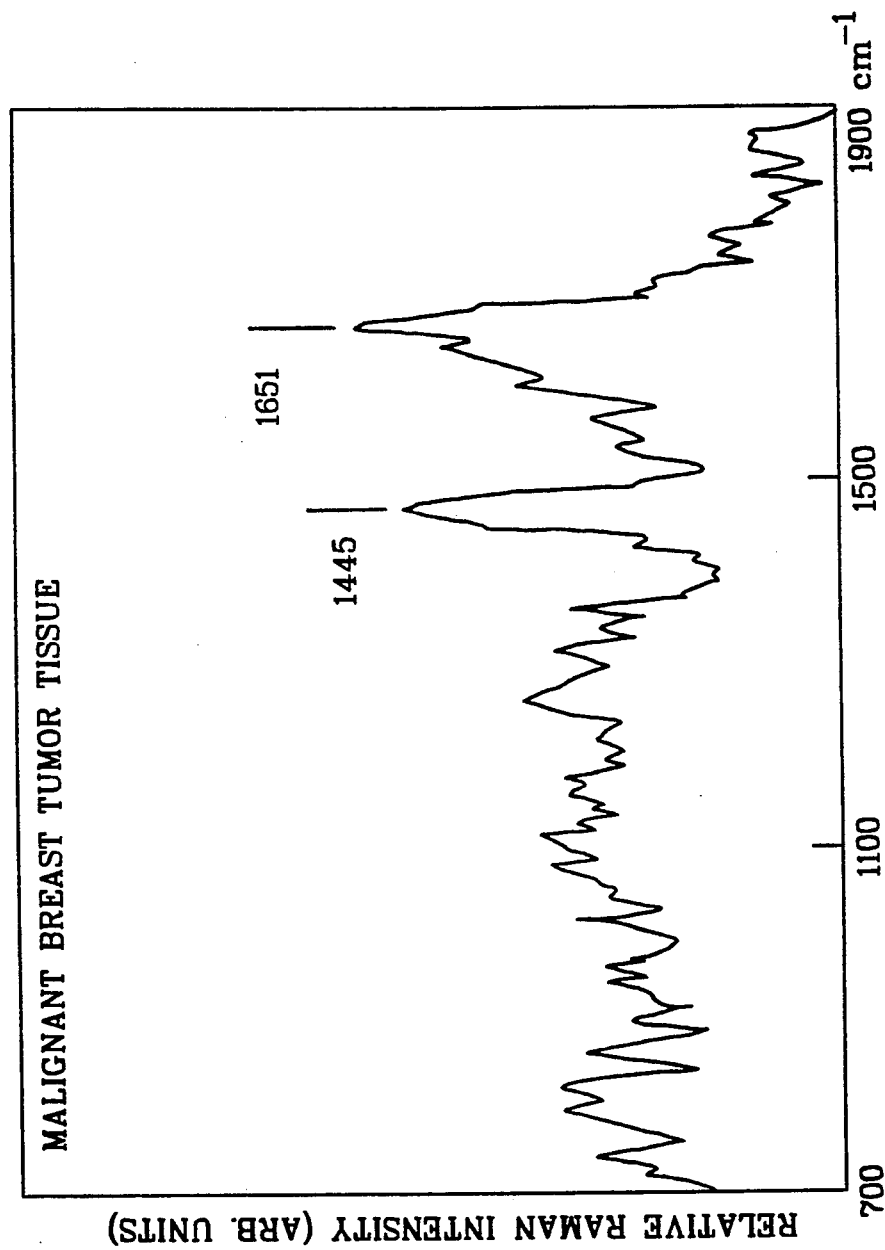
FIG. 4 is a Raman spectrum obtained from malignant tumor tissue.

Seven malignant human breast tumor tissue samples, four benign human breast tumor tissue samples, and three benign human breast tissue samples were measured with system 11. (Histology of the tissue samples were performed before the measurements.) Each tissue sample consisted of a slice having the dimensions $10 \times 6$(to 10)$\times 3$(to 8) mm. For each tissue sample, 2-3 sides and 2-5 sites/side were measured. For each measurement an area $6 \times 6$ mm was scanned for 4-5 minutes with light having a power density of about 10 watt/$cm^2$. The Raman spectral region from 700 to 1900 $cm^{-1}$ was measured at room temperature. The results of these measurements are displayed in the Table, and representative spectra for benign human breast tissue, benign human breast tumor tissue, and malignant human breast tumor tissue are depicted in FIGS. 2 through 4, respectively.

TABLE

Difference in Raman Spectra between 700 and 1900 $cm^{-1}$
for Benign Human Breast Tissue, Benign Human Breast Tumor
Tissue, and Malignant Human Breast Tissue

|  | Benign Tissue | Benign Tumor | Malignant Tumor |
| --- | --- | --- | --- |
| No. of Samples Measured | 3 | 4 | 7 |
| Measured Sites | 2-3 sides<br>2-4 sites/side | 2-3 sides<br>2-4 sites/side | 2-3 sides<br>2-4 sites/side |
| Characteristic Raman Vibrational | 1078<br>1300<br>1445, 1651 | 1240<br>1445, 1659 | 1445, 1651 |

TABLE-continued

Difference in Raman Spectra between 700 and 1900 cm$^{-1}$
for Benign Human Breast Tissue, Benign Human Breast Tumor
Tissue, and Malignant Human Breast Tissue

| | Benign Tissue | Benign Tumor | Malignant Tumor |
|---|---|---|---|
| Frequency (cm$^{-1}$) | ($\pm 4$ cm$^{-1}$) | ($\pm 4$ cm$^{-1}$) | ($\pm 4$ cm$^{-1}$) |
| Relative Intensity | $I_{(1445)} > I_{(1651)}$<br>$I_{(1078)} < I_{(1300)} < I_{(1445)} > I_{(1651)}$ | $I_{(1445)} < I_{(1651)}$ | $I_{(1445)} < I_{(1651)}$ |
| Ratio of Intensity $\frac{I_{(1445)}}{I_{(1651)}}$ | $1.25 \pm 0.09$ | $0.93 \pm 0.03$ | $0.87 \pm 0.05$ |

As can be seen from the Table and in FIGS. 2 through 4, the spectrum for benign human breast tissue is characterized by four Raman bands at a Raman shift of about 1078, 1300, 1445 and 1651 cm$^{-1}$, the spectrum for benign human breast tumor tissue is characterized by three Raman bands at a Raman shift of about 1240, 1445, and 1659 cm$^{-1}$, and the spectrum for malignant tumor tissue is characterized by two Raman bands at a Raman shift of about 1445 and 1651 cm$^{-1}$. Consequently, it is possible to characterize a sample human breast tissue as being malignant tumor tissue, benign tumor tissue, or benign (or normal) tissue, for example, by noting whether two, three, or four Raman bands appear in the spectrum or, for example, by noting whether certain Raman bands appear in the spectrum, such as the 1078 cm$^{-1}$ band, which appears only with benign human breast tissue.

As can also be seen from the Table, the ratio of intensities of the Raman bands at a Raman shift of about 1445 and 1651 cm$^{-1}$ is about 1.25 for the benign human breast tissue, about 0.93 for benign human breast tumor tissue, and about 0.87 for malignant human breast tumor tissue. Consequently, it may be possible to determine (or to rule out the possibility) that a human breast tissue sample is benign (or normal) tissue, benign tumor tissue, or malignant tumor tissue based on its intensity ratio at the two common characteristic Raman bands, namely, at a Raman shift of about 1445 and 1651 cm$^{-1}$.

Figure 5:
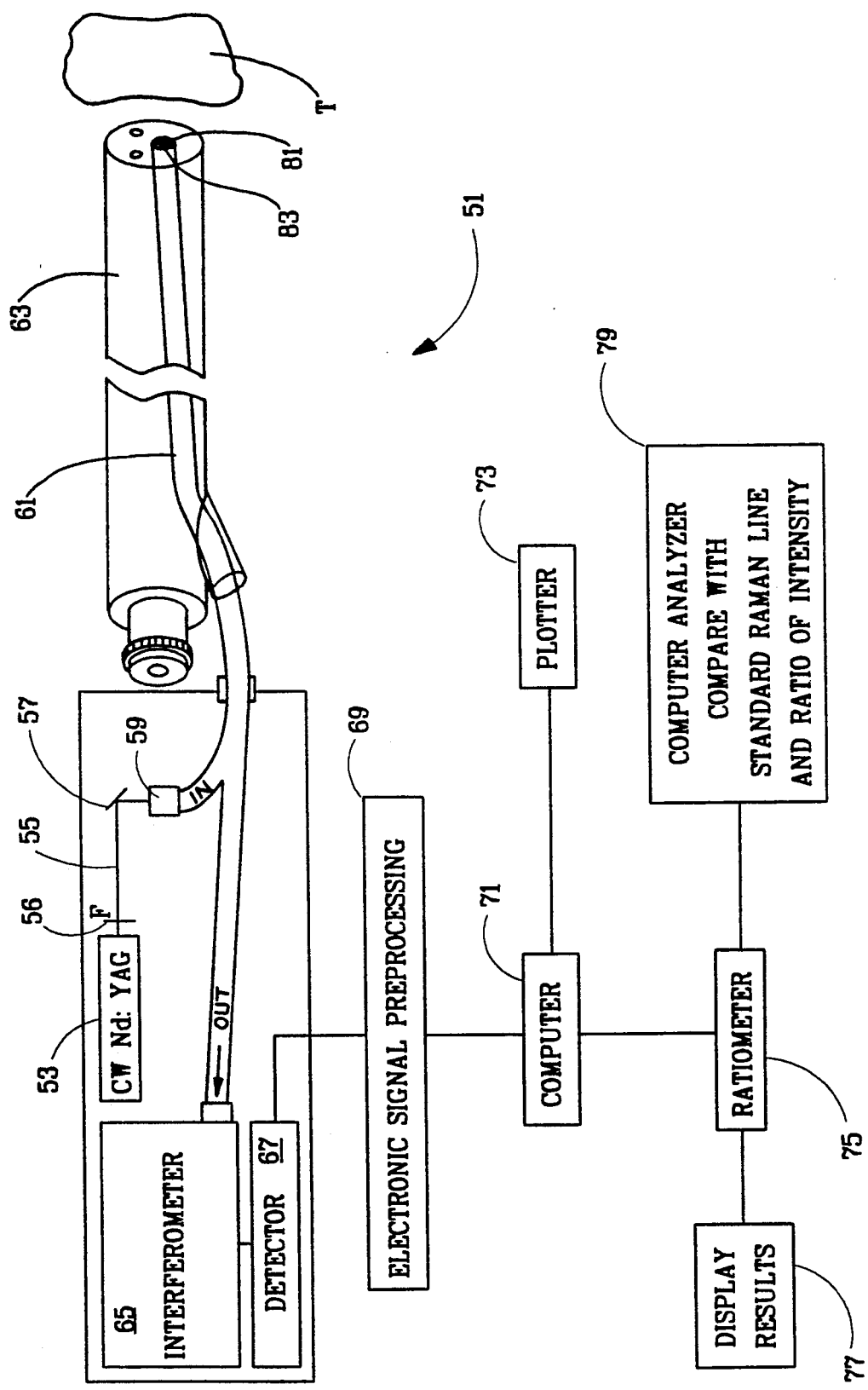
FIG. 5 is a schematic diagram of one embodiment of a device adapted for in vivo or in vitro testing of a sample tissue, the device being constructed according to the teachings of the present invention.

Referring now to FIG. 5, there is shown an embodiment of an apparatus for in vivo or in vitro testing of a tissue sample to determine if the tissue sample is a malignant tumor tissue, benign tumor tissue, or a normal or benign tissue, the apparatus being constructed according to the teachings of the present invention and represented generally by reference numeral 51.

Apparatus 51 includes a laser 53, such as a continuous wave Nd:YAG laser, for producing a beam 55 of monochromatic infrared light. Beam 55 first passes through a combination narrow-band, wide-band, neutral density filter unit 56. Next, beam 55 is reflected off a mirror 57 and passes through a lens coupler 59 into an optical fiber bundle assembly 61 disposed within a probe, which is in the form of an endoscope 63. The light strikes the tissue T being tested and produces Raman scattering. The scattered light is then transmitted back through assembly 61 into a Michelson interferometer 65. The interferogram produced by the interferometer is then detected by detector 67 and transmitted to an electronic signal preprocessing unit 69, which interfaces detector 67 to a computer 71. The output of computer 71 is then sent either to a plotter 73, which plots the Raman spectrum, or to a ratiometer 75, which calculates the ratio of intensities at two common characteristic Raman lines, such as the Raman bands at a Raman shift of about 1445 and 1651 cm$^{-1}$ in the case of human breast tissue. The output from ratiometer 75 is then sent either to a display 77 or to a computer analyzer 79, which compares the intensity ratio for the tissue being tested with standard ratios and the number of active Raman lines from malignant tumor tissue, benign tumor tissue, and normal or benign tissue.

Figure 7:
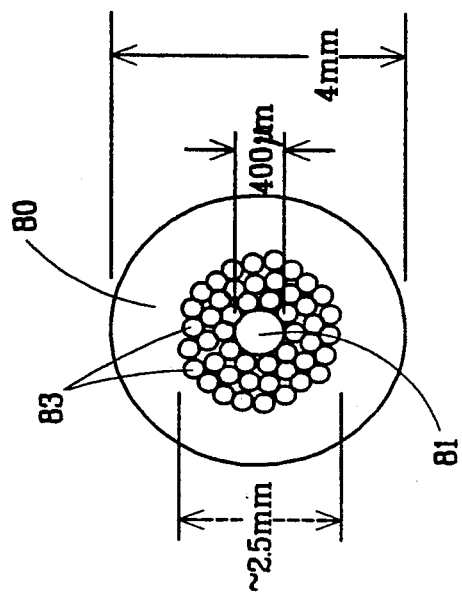
FIG. 7 is an enlarged section view taken along the line AA of the optical fiber bundle shown in FIG. 6.
Figure 6:
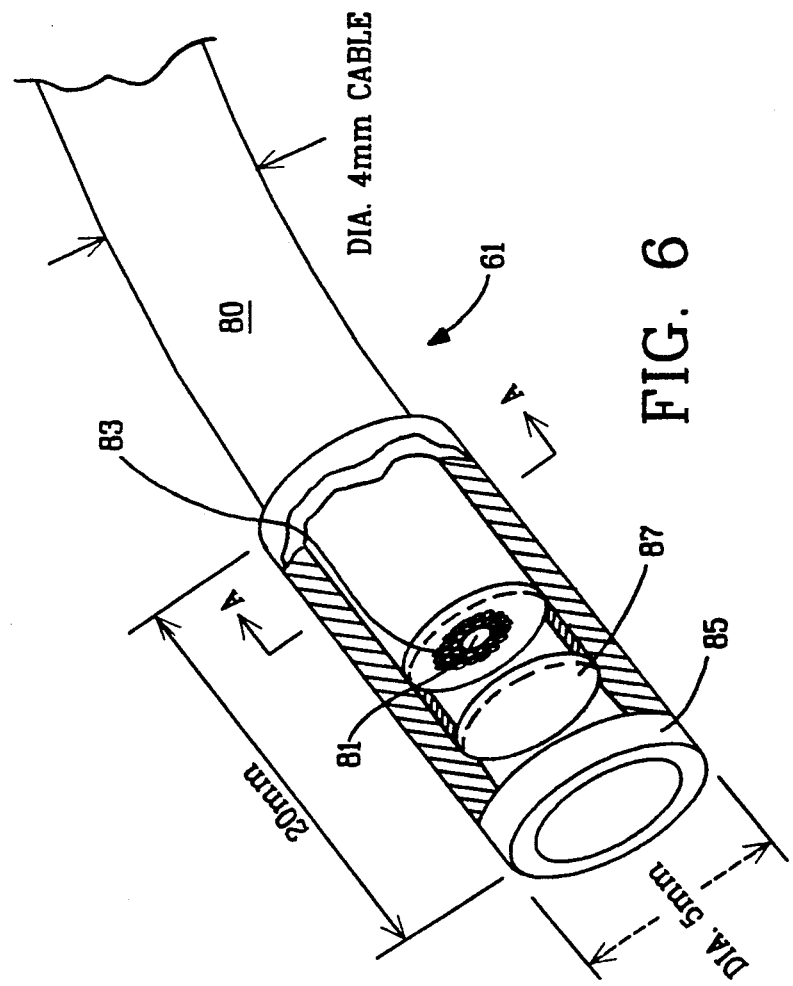
FIG. 6 is an enlarged perspective view, broken away in part, of the optical fiber bundle assembly shown in FIG. 5.

Referring now to FIG. 6, there is shown an enlarged perspective view, broken away in part, of optical fiber bundle assembly 61. Assembly 61 includes a cable 80. Cable 80, which has an outer diameter of 4 mm, houses a number of optical fibers 81 and 83 made of quartz, sapphire or any other infrared-transmitting material. Fiber 81, which is centrally disposed in cable 80, has a diameter of about 400 μm. Fiber 81 conveys the beam of infrared monochromatic light to the tissue being tested. Optical fibers 83, each having a diameter of about 100 to 200 μm, surround fiber 81. Fibers 83 convey the Raman scattered light from the tissue being tested to the interferometer. Fibers 81 and 83, taken together, have a diameter of about 2.5 to 4.0 mm (see FIG. 7).

Assembly 61 also includes a housing 85, which is glued to the end of cable 80. Housing 85, which is about 20 mm in length and about 5 mm in diameter, is preferably made of metal. If desired, a focusing lens 87 for focusing the light entering and leaving the optical fibers may be mounted within housing 85. Lens 87, which is made of quartz or sapphire, is preferably 3 mm in diameter and has a focal length of 7 mm.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method for determining if a tissue is a malignant tumor tissue, a benign tumor tissue, or a normal or benign tissue comprising the steps of:
    a) irradiating the tissue with a beam of infrared monochromatic light;
    b) obtaining the infrared Raman spectrum for the tissue in the Raman spectral region from 700 to 1900 cm$^{-1}$; and
    c) comparing said infrared Raman spectrum so obtained for the tissue with infrared Raman spectra correspondingly obtained from known samples of malignant tumor tissue, benign tumor tissue, and normal or benign tissue for the same type of tissue being tested.

2. The method of claim 1 wherein the tissue being tested is human tissue.

3. The method of claim 2 wherein the human tissue is derived from a part of the body selected from the group consisting of the vagina, the cervix, the uterus, the ovaries, the rectum, the colon, the brain, the bladder, the skin, the breast, the stomach, the lung and the mouth.

4. The method of claim 3 wherein the human tissue is derived from the breast.

5. A method of determining if a tissue is a malignant tumor tissue, a benign tumor tissue, or a benign or normal tissue, comprising the steps of:
   a) irradiating the tissue with a beam of infrared monochromatic light;
   b) measuring the number of Raman bands produced thereby in the Raman spectral region from 700 to 1900 cm$^{-1}$; and
   c) comparing said number of Raman bands measured with the number of Raman bands correspondingly measured from known samples of malignant tumor tissue, benign tumor tissue, and benign or normal tissue for the same type of tissue being tested.

6. The method of claim 5 wherein the tissue being tested is human breast tissue and wherein the number of bands is four Raman bands for benign or normal human breast tissue, three Raman bands for benign human breast tumor tissue, and two Raman bands for malignant human breast tumor tissue.

7. A method of determining if a human breast tissue sample is a malignant tumor tissue, a benign tumor tissue, or a normal or benign tissue comprising the steps of:
   a) irradiating the human breast tissue sample with a beam of infrared monochromatic light;
   b) measuring for the presence of Raman bands at a Raman shift of about 1078, 1240, and 1300 cm$^{-1}$;
   c) whereby the absence of Raman bands at a Raman shift of about 1078, 1240, and 1300 cm$^{-1}$ indicates that the human breast tissue sample is a malignant tumor tissue, the presence of a Raman band at a Raman shift of about 1240 cm$^{-1}$ and the absence of Raman bands at a Raman shift of about 1078 and 1300 cm$^{-1}$ indicates that the human breast tissue sample is a benign tumor tissue, and the presence of Raman bands at a Raman shift of about 1078 and 1300 cm$^{-1}$ and the absence of a Raman band at a Raman shift of about 1240 cm$^{-1}$ indicates that the human breast tissue sample is a normal or benign tissue.

8. A method for use in determining if a tissue of human breast is a malignant tumor tissue, a benign tumor tissue, or a normal or benign tissue comprising the steps of:
   a) irradiating the tissue with a beam of infrared monochromatic light producing thereby an infrared Raman spectrum having a first band at 1445±4 cm$^{-1}$ and a second band at a wavenumber selected from the group consisting of 1651±4 cm$^{-1}$;
   b) measuring the intensity of said first and second Raman bands so produced;
   c) calculating the ratio of said intensities; and
   d) comparing said ratio to the ratio correspondingly obtained for the same two Raman bands from known samples of malignant human breast tumor tissue, benign human breast tumor tissue, and normal or benign human breast tissue.

9. An apparatus for use in determining if a tissue is a malignant tumor tissue, a benign tumor tissue, or a normal or benign tissue comprises:
   a) means for producing an infrared monochromatic beam of light;
   b) an endoscope comprising means for transmitting the infrared monochromatic beam of light to the tissue and means for collecting the Raman scattered light from the tissue;
   c) means, coupled to said collecting means, for producing a Raman spectrum for the tissue;
   d) means for comparing the Raman spectrum for the tissue being tested to standard Raman spectra for malignant tumor tissue, benign tumor tissue, and normal or benign tissue for the same type of tissue being tested; and
   e) means for displaying the result of the comparison.

10. The apparatus of claim 9 wherein said means for producing an infrared monochromatic beam of light comprises a laser selected from the group consisting of semiconductor lasers, fosterite lasers, YAG lasers, Ti sapphire lasers, alexandrite lasers, emerald lasers, GGSG lasers, and dye lasers.

11. An apparatus for determining if human breast tissue is malignant tumor tissue, benign tumor tissue, or normal or benign tissue comprising:
   a) means for producing an infrared monochromatic beam of light;
   b) an endoscope comprising means for transmitting the infrared monochromatic beam of light to the human breast tissue and means for collecting the Raman scattered light from the human breast tissue;
   c) means, coupled to said collecting means, for detecting the presence of Raman bands at a Raman shift of about 1078, 1240, and 1300 cm$^{-1}$; and
   d) means for indicating that the human breast tissue is malignant tumor tissue if no Raman bands are detected at a Raman shift of about 1078, 1240, and 1300 cm$^{-1}$, is benign tumor tissue if a Raman band is detected at a Raman shift of about 1240 cm$^{-1}$ but not at a Raman shift of about 1078 and 1300 cm$^{-1}$, and is normal or benign tissue if Raman bands are detected at a Raman shift of about 1078 and 1300 cm$^{-1}$ but not at a Raman shift of 1240 cm$^{-1}$.

12. The apparatus of claim 11 wherein said means for producing an infrared monochromatic beam of light comprises a laser selected from the group consisting of semiconductor lasers, fosterite lasers, YAG lasers, Ti sapphire lasers, alexandrite lasers, emerald lasers, GGSG lasers, and dye lasers.

13. An apparatus for use in determining if a human breast tissue is a malignant human breast tumor breast tumor tissue, a benign human breast tumor tissue, or a normal or benign human breast tissue comprising:
   a) means for producing an infrared monochromatic beam of light;
   b) an endoscope comprising means for transmitting the infrared monochromatic beam of light to the human breast tissue and means for collecting the Raman scattered light from the human breast tissue said Raman scattered light including a first band at 1445±4 cm$^{-1}$ and a second band at a wavenumber selected from the group consisting of 1651±4 cm$^{-1}$ and 1659±4 cm$^{-1}$;
   c) means, coupled to said collecting means, for detecting the intensity of light at said first and said second bands;
   d) means for calculating the ratio of said intensities;
   e) means for comparing said ratio to ratios correspondingly obtained from known samples of malignant human breast tumor tissue, benign human breast tumor tissue, and normal or benign human breast tissue; and
   f) means for displaying the result of the comparison.

14. The apparatus of claim 13 wherein said means for producing an infrared monochromatic beam of light comprises a laser selected from the group consisting of semiconductor lasers, fosterite lasers, YAG lasers, Ti sapphire lasers, alexandrite lasers, emerald lasers, GGSG lasers, and dye lasers.

15. An apparatus for use in determining if a tissue is a malignant tumor tissue, a benign tumor tissue, or a normal or benign tissue comprising:
   a) means for producing a beam of infrared monochromatic light;
   b) an endoscope comprising means for transmitting the infrared monochromatic beam of light to the tissue and means for collecting the Raman scattered light from the tissue over the spectral region from about 700 to 1900 cm$^{-1}$;
   c) means, coupled to said collecting means, for measuring the number of Raman bands present in the Raman scattered light;
   d) means for comparing the number of Raman bands present in the Raman scattered light with standards obtained from known samples of malignant tumor tissue, benign tumor tissue, and normal or benign tissue for the same type of tissue being tested; and
   e) means for displaying the result of the comparison.

16. The apparatus of claim 15 wherein said means for producing an infrared monochromatic beam of light comprises a laser selected from the group consisting of semiconductor lasers, fosterite lasers, YAG lasers, Ti sapphire lasers, alexandrite lasers, emerald lasers, GGSG lasers, and dye lasers.

* * * * *